United States Patent

Curtze et al.

[11] 4,087,533
[45] May 2, 1978

[54] 1-(1-ACYLAMINO-2,2,3-TRICHLOROPROPYL)-IMIDAZOLES AND 1,2,4-TRIAZOLES

[75] Inventors: Jurgen Curtze, Geisenheim-Johannisberg; Klaus Thomas, Gau-Algesheim; Walter Ost, Bingen, Rhein; Christo Assenov Drandarewski, Ingelheim am Rhein, all of Germany

[73] Assignee: Celamerck GmbH & Co., KG, Ingelheim am Rhein, Germany

[21] Appl. No.: 708,883

[22] Filed: Jul. 26, 1976

[30] Foreign Application Priority Data

Jul. 29, 1975 Germany .............................. 2533792
Jan. 26, 1976 Germany .............................. 2602739

[51] Int. Cl.$^2$ ...................... C07D 249/08; A01N 9/22
[52] U.S. Cl. ................................. 424/269; 260/308 R; 260/347.3; 260/557 R; 260/558 R; 260/559 B; 260/561 R; 260/561 N; 260/561 HL; 424/273 R; 542/421; 548/336; 548/341
[58] Field of Search ...................... 260/308 R, 240 R; 424/269

[56] References Cited

U.S. PATENT DOCUMENTS 3,707,477  12/1972  Ost et al. .............................. 260/309

*Primary Examiner*—Raymond V. Rush
*Attorney, Agent, or Firm*—Hammond & Littell

[57] ABSTRACT

Compounds of the formula

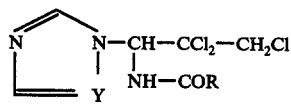

wherein
R is hydrogen, alkyl of 1 to 12 carbon atoms, mono- or di-halo(alkyl of 1 to 12 carbon atoms), phenoxy (alkyl of 1 to 12 carbon atoms), lower alkyl-phenoxy(alkyl of 1 to 12 carbon atoms), halo-phenoxy (alkyl of 1 to 12 carbon atoms), phenyl(alkyl of 1 to 12 carbon atoms), halo-phenyl(alkyl of 1 to 12 carbon atoms), lower alkyl-phenyl(alkyl of 1 to 12 carbon atoms), lower alkoxy-phenyl(alkyl of 1 to 12 carbon atoms), lower alkenyl, phenyl-lower alkenyl, phenyl, halo-phenyl, nitro-phenyl, lower alkoxy, furyl or cycloalkyl, and
Y is nitrogen or =CH—;
the compounds are useful as fungicides.

3 Claims, No Drawings

1-(1-ACYLAMINO-2,2,3-TRICHLORO-PROPYL)-IMIDAZOLES AND 1,2,4-TRIAZOLES

This invention relates to novel 1-(1-acylamino-2,2,3-trichloro-n-propyl)-imidazoles and -1,2,4-triazoles, as well as to methods of preparing these compounds.

More particularly, the present invention relates to a novel class of N-substituted imidazoles and triazoles represented by the formula

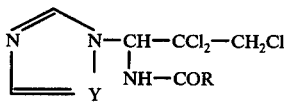

(I)

wherein
R is hydrogen, alkyl of 1 to 12 carbon atoms, mono- or di-halo(alkyl of 1 to 12 carbon atoms), phenoxy(alkyl of 1 to 12 carbon atoms), lower alkyl-phenoxy(alkyl of 1 to 12 carbon atoms), halo-phenoxy(alkyl of 1 to 12 carbon atoms), phenyl(alkyl of 1 to 12 carbon atoms), halo-phenyl(alkyl of 1 to 12 carbon atoms), lower alkyl-phenyl(alkyl of 1 to 12 carbon atoms), lower alkoxy-phenyl(alkyl of 1 to 12 carbon atoms), lower alkenyl, phenyl-lower alkenyl, phenyl, halo-phenyl, nitro-phenyl, lower alkoxy, furyl or cycloalkyl, and
Y is nitrogen or =CH—.

The compounds embraced by formula I may be prepared by the following methods:

METHOD A

By reacting a compound of the formula

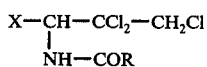

(II)

wherein
R has the same meanings as in formula I, and
X is a substituent which can be split off as an anion, such as chlorine, bromine, acyloxy, arylsulfonyloxy or alkylsulfonyloxy,
with imidazole or 1,2,4-triazole.

The reaction is advantageously carried out in an inert organic solvent, such as tetrahydrofuran, dioxane, toluene, acetone or a chlorinated hydrocarbon, and in the presence of a basic compound. Examples of suitable basic compounds are organic bases, for instance tertiary amines such as triethylamine, as well as moderately strong basic inorganic compounds such as sodium carbonate. The operative reaction temperature range is between −20° and +100° C, but it is preferred to perform the reaction between +10° and +40° C because it readily proceeds at room temperature.

The reactants are preferably provided in a molar ratio of 1:1, although the imidazole of 1,2,4-triazole may also be provided in excess, in which case the excess amount may serve to tie up the acid which is released by the reaction.

The starting compounds of the formula II may be obtained by replacing the 1-hydroxyl substituent in an N-(1-hydroxy-2,2,3-trichloro-n-propyl)-acid amide by substituent X, as defined above, pursuant to known methods. Some of the required N-(1-hydroxy-2,2,3-trichloro-n-propyl)-acid amides are described in the literature, while the others may be obtained from 2,2,3-trichloro-propionaldehyde and the corresponding acid amide in a manner analogous to that for the preparation of the known compounds.

METHOD B

By reacting an aldimine of the formula

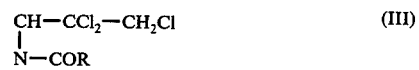

(III)

wherein R has the same meanings as in formula I, with imidazole or 1,2,4-triazole.

The reactants are preferably provided in a molar ration of 1:1, and the reaction is carried out under the same conditions as in method A, except that the presence of an acid-binding agent is not required.

The starting compounds of the formula III may be prepared by the method described in J. prakt. Chem. 316, 63–66 (1974) or in ananlogous manner.

The following examples illustrate the present invention and will enable others skilled in the art to understand it more completely. It should be understood, however, that the invention is not limited solely to the particular examples given below.

PREPARATION OF STARTING COMPOUNDS

N-(1-hydroxy-2,2,3-trichloro-n-propyl)-formamide

A mixture consisting of 16.2 gm of 2,2,3-trichloropropionaldehyde and 4.5 gm of formamide was stirred on a boiling water bath for 30 minutes. Recrystallization of the reaction product from benzene yielded 17 gm of the desired compound, m.p. 105°–109° C.

Analogous to J. prakt. Chem. 316 (1974), pages 63–66, the following N-(1-hydroxy-2,2,3-trichloro-n-propyl)-acid amides were also prepared:
N-(1-hydroxy-2,2,3-trichloro-n-propyl)-acetamide, m.p. 70°–72° C;
N-(1-hydroxy-2,2,3-trichloro-n-propyl)-propionamide, m.p. 145°–147° C;
N-(1-hydroxy-2,2,3-trichloro-n-propyl)-n-butyric acid amide, m.p. 129° C;
N-(1-hydroxy-2,2,3-trichloro-n-propyl)-isobutyric acid amide, m.p. 132° C;
N-(1-hydroxy-2,2,3-trichloro-n-propyl)-pivalic acid amide, m.p. 126° C;
N-(1-hydroxy-2,2,3-trichloro-n-propyl)-enanthic acid amide, m.p. 122° C;
N-(1-hydroxy-2,2,3-trichloro-n-propyl)-lauric acid amide, m.p. 92° C;
N-(1-hydroxy-2,2,3-trichloro-n-propyl)-acrylic acid amide, m.p. 146° C;
N-(1-hydroxy-2,2,3-trichloro-n-propyl)-methacrylic acid amide, m.p. 120° C;
N-(1-hydroxy-2,2,3-trichloro-n-propyl)-3-methylcrotonic acid amide, m.p. 142° C;
N-(1-hydroxy-2,2,3-trichloro-n-propyl)-phenylacetamide, m.p. 120° C;
N-(1-hydroxy-2,2,3-trichloro-n-propyl)-hydrocinnamic acid amide, m.p. 123° C;
N-(1-hydroxy-2,2,3-trichloro-n-propyl)-diphenylacetamide, m.p. 153° C;
N-(1-hydroxy-2,2,3-trichloro-n-propyl)-cinnamic acid amide, m.p. 156° C;
N-(1-hydroxy-2,2,3-trichloro-n-propyl)-cyclopropanecarboxylic acid amide, m.p. 146° C;
N-(1-hydroxy-2,2,3-trichloro-n-propyl)-chloroacetamide, m.p. 149° C;

N-(1-hydroxy-2,2,3-trichloro-n-propyl)-dichloroacetamide, m.p. 85° C;

N-(1-hydroxy-2,2,3-trichloro-n-propyl)-3-chloropropionamide, m.p. 144° C;

N-(1-hydroxy-2,2,3-trichloro-n-propyl)-2-chlorobenzamide, m.p. 138° C;

N-(1-hydroxy-2,2,3-trichloro-n-propyl)-4-chlorobenzamide, m.p. 140° C;

N-(1-hydroxy-2,2,3-trichloro-n-propyl)-phenoxyacetamide, m.p. 155° C;

N-(1-hydroxy-2,2,3-trichloro-n-propyl)-2,4-dichlorophenoxyacetamide, m.p. 102° C;

N-(1-hydroxy-2,2,3-trichloro-n-propyl)-3-phenoxypropionamide, m.p. 97° C;

N-(1-hydroxy-2,2,3-trichloro-n-propyl)-furan-2-carboxylic acid amide, m.p. 147° C;

N-(1-hydroxy-2,2,3-trichloro-n-propyl)-methyl-carbaminate, m.p. 139°–143° C;

N-(1-hydroxy-2,2,3-trichloro-n-propyl)-2-methyl-4-chlorophenoxy-acetic acid amide, m.p. 111°–118° C; and N-(1-hydroxy-2,2,3-trichloro-n-propyl)-chloropivalic acid amide, m.p. 102°–108° C.

PREPARATION OF END PRODUCTS OF THE FORMULA I

EXAMPLE 1

(a) N-(1,2,2,3-tetrachloropropyl)-acetamide 30 ml of thionyl chloride were poured over 15 gm of N-(1-hydroxy-2,2,3-trichloro-n-propyl)-acetamide, and the mixture was refluxed until the solution became clear. Subsequently, the excess thionyl chloride was distilled off in vacuo, and the residue was recrystallized from benzene/petroleum ether. Upon washing of the crystallizate with petroleum ether, a colorless substance was obtained. Yield: 13.5 gm; m.p. 70°–72° C.

(b) 1-(1-Acetamino-2,2,3-trichloro-n-propyl)-1,2,4-triazole by method A 3.6 gm of N-(1,2,2,3-tetrachloro-n-propyl)-acetamide were dissolved in 30 ml of tetrahydrofuran, and, while stirring, the resulting solution was added dropwise to a solution of 1.05 gm of 1,2,4-triazole and 1.8 gm of triethylamine in 20 ml of tetrahydrofuran. Subsequently, the reaction mixture was stirred for 2 hours at room temperature, then water was added, and the tetrahydrofuran was distilled off in vacuo. The oil thus obtained as a residue crystallized after some time and was recrystallized from methanol/water, yielding 2.7 gm of the compound of the formula

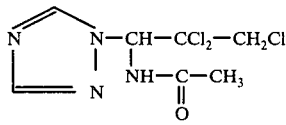

having a melting point of 135° C.

EXAMPLE 2

(a) N-acetyl-2,2,3-trichloro-n-propionaldimine 16.0 gm of N-(1,2,2,3-tetrachloro-n-propyl)-acetamide were dissolved in 100 ml of toluene, and, while stirring, a solution of 6.76 gm of triethylamine in 50 ml of toluene was added dropwise thereto. The mixed solution was stirred for 30 minutes, and then the triethylamine hydrochloride which had separated out was suction-filtered off. The filtrate was evaporated in vacuo, and the residue was fractionally distilled in vacuo. Yield: 7.0 gm; b.p. 65° C/0.1 mm Hg.

(b) 1-(1-Acetamino-2,2,3-trichloro-n-propyl)-1,2,4-triazole by method B 1.73 gm of 1,2,4-triazole were dissolved in 10 ml of absolute tetrahydrofuran, and, while stirring, a solution of 5.06 gm of N-acetyl-2,2,3-trichloro-propionaldimine in 20 ml of absolute tetrahydrofuran was added dropwise thereto. The mixed solution was refluxed for 30 minutes. Upon evaporating the reaction solution and then admixing the residue with water, a slowly crystallizing oil was obtained which was recrystallized from methanol/water. Yield: 5.8 gm; m.p. 135° C.

EXAMPLE 3

1-(1-Propionylamino-2,2,3-trichloro-n-propyl)-1,2,4-triazole by method A 5.8 gm of N-(1-hydroxy-2,2,3-trichloropropyl)-propionamide were admixed with 20 ml of thionyl chloride, and the mixture was refluxed for 30 minutes. Subsequently, the reaction mixture was evaporated in vacuo. The crude N-(1,2,2,3-tetrachloro-n-propyl)-propionamide thus obtained was dissolved in 30 ml of tetrahydrofuran, and, while stirring, the solution was added to a solution of 1.75 gm of 1,2,4-triazole and 4.2 ml of triethylamine in 30 ml of tetrahydrofuran. After standing for 3 hours at room temperature, the reaction solution was admixed with water, and the tetrahydrofuran was distilled off in vacuo. A quickly solidifying oil was obtained, and the crystallizate was recrystallized from methanol/water. Yield: 4.6 gm; m.p. 167° C.

Using procedures analogous to those described in the preceding examples, the following compounds of the formula I were also prepared:

1-(1-Formylamino-2,2,3-trichloro-n-propyl)-1,2,4-triazole, m.p. 112° C;

1-(1-Acetamino-2,2,3-trichloro-n-propyl)-1,2,4-triazole, m.p. 135° C;

1-(1-Propionylamino-2,2,3-trichloro-n-propyl)-1,2,4-triazole, m.p. 167° C;

1-(1-Butyrylamino-2,2,3-trichloro-n-propyl)-1,2,4-triazole, m.p. 106° C;

1-(1-Isobutyrylamino-2,2,3-trichloro-n-propyl)-1,2,4-triazole, m.p. 153° C;

1-(1-Heptanoylamino-2,2,3-trichloro-n-propyl)-1,2,4-triazole, m.p. 102° C;

1-(1-Lauroylamino-2,2,3-trichloro-n-propyl)-12,4-triazole, m.p. 80° C;

1-(1-Methacrylamino-2,2,3-trichloro-n-propyl)-12,4-triazole, m.p. 108° C;

1-[1-(3-Methylcrotonyl-amino)-2,2,3-trichloro-n-propyl]-1,2,4-triazole, m.p. 152° C;

1-(1-Phenylacetamino-2,2,3-trichloro-n-propyl)-1,2,4-triazole, m.p. 147° C;

1-[1-(3-Phenylpropionyl-amino)-2,2,3-trichloro-n-propyl]-1,2,4-triazole, m.p. 90° C;

1-(1-Diphenylacetamino-2,2,3-trichloro-n-propyl)-1,2,4-triazole, m.p. 178° C;

1-(1-Cinnamoylamino-2,2,3-trichloro-n-propyl)-1,2,4-triazole, m.p. 159° C;

1-(1-Cyclopropylcarbamino-2,2,3-trichloro-n-propyl)-1,2,4-triazole, m.p. 152° C;

1-(1-Chloroacetamino-2,2,3-trichloro-n-propyl)-1,2,4-triazole, m.p. 150° C;
1-(1-Dichloroacetamino-2,2,3-trichloro-n-propyl)-1,2,4-triaole, m.p. 202° C;
1-[1-(3-Chloropropionyl-amino)-2,2,3-trichloro-n-propyl]-1,2,4-triazole, m.p. 134° C;
1-[1-(2-Chlorobenzoyl-amino)-2,2,3-trichloro-n-propyl]-1,2,4-triazole, m.p. 160° C;
1-[1-(4-Chlorobenzoyl-amino)-2,2,3-trichloro-n-propyl]-1,2,4-triazole, m.p. 165° C;
1-(1-Phenoxyacetamino-2,2,3-trichloro-n-propyl)-1,2,4-triazole, m.p. 135° C;
1-[1-(2-Dichlorophenoxy-acetamino)-2,2,3-trichloro-n-propyl]-1,2,4-triazole, m.p. 150° C;
1-[1-(3-Phenoxypropionyl-amino)-2,2,3-trichloro-n-propyl]-1,2,4-triazole, m.p. 168° C;
1-[1-(Furan-2-carbamino)-2,2,3-trichloro-n-propyl]-1,2,4-triazole, m.p. 128° C;
1-(1-Carbomethoxyamino-2,2,3-trichloro-n-propyl)-1,2,4-triazole, m.p. 152° C;
1-[1-(2-Methyl-4-chlorophenoxy-acetamino)-2,2,3-trichloro-n-propyl]-1,2,4-triazole, m.p. 117°-120° C;
1-(1-Chloropivaloylamino-2,2,3-trichloro-n-propyl)-1,2,4-triazole, m.p. 101°-104° C;
1-(1-Benzoylamino-2,2,3-trichloro-n-propyl)-1,2,4-triazole;
1-[1-(2-Bromobenzoyl-amino)-2,2,3-trichloro-n-propyl]-1,2,4-triazole, m.p. 143°-145° C;
1-[1-(2,4-Dichlorobenzoyl-amino)-2,2,3-trichloro-n-propyl]-1,2,4-triazole, m.p. 160°-162° C;
1-[1-(3,5-Dichlorobenzoyl-amino)-2,2,3-trichloro-n-propyl]-1,2,4-triazole, m.p. 115°-119° C;
1-[1-(4-Nitrobenzoyl-amino)-2,2,3-trichloro-n-propyl]-1,2,4-triazole, m.p. 133°-136° C;
1-[1-(2-Methylbenzoyl-amino)-2,2,3-trichloro-n-propyl]-1,2,4-triazole;
1-[1-(4-Methylbenzoyl-amino)-2,2,3-trichloro-n-propyl]-1,2,4-triazole, m.p. 133°-137° C;
1-[1-(2-Methoxybenzoyl-amino)2,2,3-trichloro-n-propyl]-1,2,4-triazole, m.p. 145°-148° C;
1-[1-(2,4-Dimethoxybenzoyl-amino)-2,2,3-trichloro-n-propyl]-1,2,4-triazole, m.p. 133°-136° C;
1-[1-(3,4,5-Trimethoxybenzoyl-amino)-2,2,3-trichloro-n-propyl]-1,2,4-triazole, m.p. 171°-173° C;
1-[1-(2-Ethylbutyryl-amino)-2,2,3-trichloro-n-propyl]-1,2,4-triazole, m.p. 130°-140° C;
1-[1-(2-Chloropropionyl-amino)-2,2,3-trichloro-n-propyl]-1,2,4-triazole, m.p. 160°-163° C;
1-(1-Pivaloylamino-2,2,3-trichloro-n-propyl)-1,2,4-triazole, m.p. 72°-77° C;
1-[1-(4-Chlorobutyryl-amino)-2,2,3-trichloro-n-propyl]-1,2,4-triazole, m.p. 108°-114° C; and
1-[1-(2-Methyl-n-valeroyl-amino)-2,2,3-trichloro-n-propyl]-1,2,4-triazole, m.p. 77°-85° C.

EXAMPLE 4

(a) N-(1,2,2,3-tetrachloro-n-propyl)-formamide

Thionyl chloride was poured over 20.6 gm of N-(1-hydroxy-2,2,3-trichloro-n-propyl)-formamide, and the mixture was refluxed for 15 minutes. Subsequently, the excess thionyl chloride was distilled off, and the residue was recrystallized from benzene/petroleum ether, m.p. 55°-57° C.

(b) 1-(1-Formamino-2,2,3-trichloro-n-propyl)-imidazole by method A 4.5 gm of N-(1,2,2,3-tetrachloro-n-propyl)-formamide were dissolved in 30 ml of tetrahydrofuran, and the resulting solution was added dropwise to a solution of 1.36 gm of imidazole and 2.4 gm of triethylamine in 20 ml of tetrahydrofuran. The mixture was stirred for 2 hours, whereupon water was added and the tetrahydrofuran was distilled off in vacuo. The precipitated oil crystallized after some time, yielding 4 gm of crystallizate. After recrystallization from ethanol a colorless crystalline substance, m.p. 134°-137° C, was obtained, which was identified to be the compound of the formula

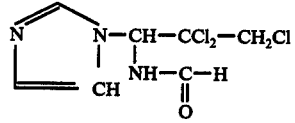

EXAMPLE 5

1-(1-Propionylamino-2,2,3-trichloro-n-propyl)-imidazole by method A 7.05 gm of N-(1-hydroxy-2,2,3-trichloro-n-propyl)-propionamide were admixed with 25 ml of thionyl chloride and the mixture was refluxed for 30 minutes. Subsequently, the reaction solution was evaporated in vacuo, and the residual crude N-(1,2,2,3-tetrachloro-n-propyl)-propionamide was dissolved in 25 ml of tetrahydrofuran. The resulting solution was added dropwise to 50 ml of a solution of 2.05 gm of imidazole and 5 ml of triethylamine in tetrahydrofuran. The mixture was stirred for 2 hours, and then water was added and the tetrahydrofuran was distilled off in vacuo. The residual oil was recrystallized from methanol/water. Yield: 6 gm; m.p. 163° C.

The following compounds were prepared in analogous manner:
1-(1-Acetamino-2,2,3-trichloro-n-propyl)-imidazole, m.p. 151°-154° C;
1-(1-n-Butyrylamino-2,2,3-trichloro-n-propyl)-imidazole, m.p. 127° C;
1-(1-Dichloroacetamino-2,2,3-trichloro-n-propyl)-imidazole, m.p. 169° C;
1-[1-(3-Chloropropionyl-amino)-2,2,3-trichloro-n-propyl]-imidazole, m.p. 124° C;
1-(1-Isobutyrylamino-2,2,3-trichloro-n-propyl)-imidazole, m.p. 141° C;
1-(1-Acrylamino-2,2,3-trichloro-n-propyl)-imidazole, m.p. 200° C (decomp.);
1-(1-Methacrylamino-2,2,3-trichloro-n-propyl)-imidazole, m.p. 127° C;
1-(1-Cyclopropylcarbamino-2,2,3-trichloro-n-propyl)-imidazole, m.p. 145° C;
1-(1-Carbomethoxyamino-2,2,3-trichloro-n-propyl)-imidazole, m.p. 153° C;
1-(1-Carbethoxyamino-2,2,3-trichloro-n-propyl)-imidazole, m.p. 90°-93° C;
1-[1-(2,6-Dichlorobenzoyl-amino)-2,2,3-trichloro-n-propyl]-imidazole, m.p. 213° C;
1-[1-(3-Phenoxypropionyl-amino)-2,2,3-trichloro-n-propyl]-imidazole, m.p. 135° C;
1-[1-(3-Phenylpropionyl-amino)-2,2,3-trichloro-n-propyl]-imidazole, m.p. 149° C;
1-(1-Furyl-2-carbamino-2,2,3-trichloro-n-propyl)-imidazole, m.p. 162° C;
1-(1-Phenoxyacetamino-2,2,3-trichloro-n-propyl)-imidazole, m.p. 137° C;

1-(1-Phenylacetamino-2,2,3-trichloro-n-propyl)-
imidazole, m.p. 151° C;
1-(1-n-Valeroylamino-2,2,3-trichloro-n-propyl)-
imidazole, m.p. 133° C;
1-[1-(2-chloropropionyl-amino)-2,2,3-trichloro-n-
propyl]-imidazole, m.p. 120°–124° C;
1-[1-(4-Methylbutyryl-amino)-2,2,3-trichloro-n-
propyl]-imidazole, m.p. 158° C;
1-[1-(3-Phenylacrylamino)-2,2,3-trichloro-n-propyl]-
imidazole, m.p. 192° C;
1-(1-Cyclohexylcarbamino)-2,2,3-trichloro-n-propyl)-
imidazole, m.p. 167° C;
1-(1-n-Heptylcarbamino-2,2,3-trichloro-n-propyl)-
imidazole, m.p. 145° C;
1-(1-Lauroylamino-2,2,3-trichloro-n-propyl)-imidazole,
m.p. 98° C;
1-[1-(2,4-Dichlorophenoxy-acetamino)-2,2,3-trichloro-
n-propyl]-imidazole, m.p. 148° C;
1-(1-Crotylamino-2,2,3-trichloro-n-propyl)-imidazole,
m.p. 168° C;
1-[1-(3-Methylcrotyl-amino)-2,2,3-trichloro-n-propyl]-
imidazole, m.p. 182° C;
1-[1-(2-Methylbenzoyl-amino)-2,2,3-trichloro-n-
propyl]-imidazole, m.p. 161° C;
1-[1-(2-Chlorobenzoyl-amino)-2,2,3-trichloro-n-
propyl]-imidazole, m.p. 207° C;
1-[1-(2-Chloro-4-methylphenoxy-acetamino)-2,2,3-tri-
chloro-n-propyl]-imidazole, m.p. 138°–141° C;
1-(1-Chloropivaloylamino-2,2,3-trichloro-n-propyl)-
imidazole, m.p. 113°–116° C;
1-[1-(3,4,5-trimethoxybenzoyl-amino)-2,2,3-trichloro-n-
propyl]-imidazole, m.p. 91°–95° C;
1-[1-(2,4-Dichlorobenzoyl-amino)-2,2,3-trichloro-n-
propyl]-imidazole, m.p. 173°–178° C;
1-[1-(3,5-Dichlorobenzoyl-amino)-2,2,3-trichloro-n-
propyl]-imidazole, m.p. 140°–145° C;
1-[1-(2-Methoxybenzoyl-amino)-2,2,3-trichloro-n-
propyl]-imidazole, m.p. 144°–146° C;
1-[1-(2-Methyl-n-valeroyl-amino)-2,2,3-trichloro-n-
propyl]-imidazole, m.p. 134°–137° C;
1-[1-(4-Nitrobenzoyl-amino)-2,2,3-trichloro-n-propyl]-
imidazole, m.p. 187°–200° C (decomp.);
1-[1-(2-Bromobenzoyl-amino)-2,2,3-trichloro-n-
propyl]-imidazole, m.p. 178°–185° C;
1-[1-(4-Chloro-n-butyryl-amino)-2,2,3-trichloro-n-
propyl]-imidazole, m.p. 147°–149° C; and
1-[1-(2-Ethylbutyryl-amino)-2,2,3-trichloro-n-propyl]-
imidazole, m.p. 160°–162° C.

EXAMPLE 6

1-(1-Acetamino-2,2,3-trichloro-n-propyl)-imidazole by method B 6.08 gm of N-acetyl-2,2,3-trichloro-propionaldimine were dissolved in 40 ml of tetrahydrofuran, and a solution of 2.05 gm of imidazole in 30 ml of tetrahydrofuran was added dropwise thereto over a period of 5 minutes. The mixed solution was allowed to stand for 2 hours, whereupon the tetrahydrofuran was evaporated. The residue was recrystallized from tetrahydrofuran. M.p. 151°–154° C.

The following compounds were prepared in analogous manner:

1-(1-Formylamino-2,2,3-trichloro-n-propyl)-imidazole,
m.p. 134°–137° C;
1-(1-Propionylamino-2,2,3-trichloro-n-propyl)-
imidazole, m.p. 163° C;
(1-(1-n-Butyrylamino-2,2,3-trichloro-n-propyl)-
imidazole, m.p. 127° C;
1-(1-Dichloroacetamino-2,2,3-trichloro-n-propyl)-
imidazole, m.p 169° C;
1-[1-(3-Chloropropionyl-amino)-2,2,3-trichloro-n-
propyl]-imidazole, m.p. 124° C;
1-(1-Isobutyrylamino-2,2,3-trichloro-n-propyl)-
imidazole, m.p. 141° C;
1-(1-Acrylamino-2,2,3-trichloro-n-propyl)-imidazole,
m.p. 200° C (decomp.);
1-(1-Methacrylamino-2,2,3-trichloro-n-propyl)-
imidazole, m.p. 127° C; and
1-(1-Cyclopropylcarbamino-2,2,3-trichloro-n-propyl)-
imidazole, m.p. 145° C.

The compounds of the present invention, that is, those embraced by formula I above, have useful properties. More particularly, they exhibit fungicidal activity against mainly phytopathogenic fungi, especially true mildew fungi, such as Erysiphe graminis and Erysiphe cichoracearum, as well such as erysiphe graminis and Erysiphe cichoracearum, as well as against pathogenic fungi which occur in warm-blooded animals.

In addition, the compounds of this invention are useful as intermediates for the preparation of pesticides.

Particularly effective for combatting phytopathogenic fungi are those compounds of the formula I wherein R is hydrogen, β-chloro-ethyl, benzyl or methyl.

The compounds of this invention can be used for curative as well as prophylactic antifungal purposes, and they are effective when applied to the soil in which the plants grow, as well as when applied directly to the plants.

For use as agricultural and horticultural fungicides the compounds of this invention are incorporated as active ingredients into conventional compositions suitable for this purpose, that is, disseminatable compositions consisting essentially of an inert liquid or solid carrier and an effective fungicidal amount of the active ingredient, such as solutions, suspensions, emulsions concentrates, dusting powders, granulates, sprays or the like.

The active ingredient content of these compositions may be from 0.05 to 80% by weight, preferably up to 50% by weight, based on the total weight. Watermiscible concentrates are diluted with water prior to use to an active ingredient concentration of about 0.5 to 0.001% by weight. Dusting powders may have an even higher active ingredient concentration than that indicated above. The upper limit of active ingredient concentration in any of these compositions is substantially predicated upon the phytotoxicity of the active ingredient, which is relatively low in the case of the compounds of this invention.

The following examples illustrate a few agricultural or horticultural antifungal compositions containing a compound of the present invention as the active ingredient. The parts are parts by weight.

EXAMPLE 7

Wettable suspension powder

The powder is compounded from the following ingredients:

| | |
|---|---|
| 1-(1-Acetamino-2,2,3-trichloro-n-propyl)-1,2,4-triazole | 20 parts |
| Kaolin | 20 parts |

-continued

| | |
|---|---|
| Sodium sulfate | 5 parts |
| Prepared chalk | 2 |
| Calcium lignin sulfonate (dispersant) | 9 parts |
| Diisobutylnaphthalene sodium sulfonate (wetting agent) | 1 parts |
| Colloidal silicic acid | 43 parts |
| Total | 100 parts |

Preparation:

The ingredients are admixed, and the mixture is milled into a homogeneous powder. Prior to use, the powder is suspended in a sufficient amount of water to make the active ingredient concentration in the aqueous suspension from 0.001 to 0.5% by weight.

EXAMPLE 8

Aerosol spray

The spray is compounded from the following ingredients:

| | |
|---|---|
| 1-(1-Acetamino-2,2,3-trichloro-n-propyl)-imidazole | 0.05 parts |
| Sesame oil | 0.10 parts |
| N-Methyl-pyrrolidine 10.00 | parts |
| Propellant gas mixture (e.g. frigens) | 89.85 parts |
| Total | 100.00 parts |

Preparation:

The ingredients are admixed, and the mixture is filled into aerosol spray containers in conventional manner.

EXAMPLE 9

Dusting powder

The powder is compounded from the following ingredients:

| | |
|---|---|
| 1-(1-Formamino-2,2,3-trichloro-n-propyl)-imidazole | 1 parts |
| Talcum | 98 " |
| Methyl cellulose | 1 " |
| Total | 100 parts |

Preparation:

The ingredients are admixed, and the mixture is milled into a homogeneous powder.

EXAMPLE 10

Emulsion concentrate

The concentrate is compounded from the following ingredients:

| | |
|---|---|
| 1-(1-Acetamino-2,2,3-trichloro-n-propyl)-imidazole | 15 parts |
| Triethylamine salt of dodecylbenzone-sulfonic acid | 10 parts |
| Dimethylformamide | 75 parts |
| Total | 100 parts |

Preparation:

The ingredients are admixed and homogeneously blended and prior to use the resulting emulsion is diluted with water to the desired active ingredient concentration.

Any one of the other compounds embraced by formula I may be substituted for the particular active ingredient in Examples 7 through 10. Likewise, the amount of active ingredient in these illustrative examples may be varied, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 1-(1-Acetamino-2,2,3-trichloro-n-propyl)-1,2,4-triazole.

2. A fungicidal composition for combatting phytopathogenic fungi, said composition consisting essentially of an inert carrier and an effective fungicidal amount of the compound of claim 1.

3. The method of combatting phytopathogenic fungi which comprises contacting said fungi with an effective fungicidal amount of the compound of claim 1.

* * * * *